(12) United States Patent
El-Amin et al.

(10) Patent No.: US 6,830,935 B1
(45) Date of Patent: *Dec. 14, 2004

(54) METHOD FOR MIXING AND PROCESSING SPECIMEN SAMPLES

(75) Inventors: Marianna El-Amin, Bethesda, MD (US); Raouf A. Guirguis, Vienna, VA (US); Nashed Samaan, Germantown, MD (US)

(73) Assignee: LaMina, Inc., Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/720,543

(22) PCT Filed: Jul. 7, 1999

(86) PCT No.: PCT/US99/15281

§ 371 (c)(1),
(2), (4) Date: Jun. 25, 2001

(87) PCT Pub. No.: WO00/02031

PCT Pub. Date: Jan. 13, 2001

Related U.S. Application Data

(60) Provisional application No. 60/092,029, filed on Jul. 7, 1998.

(51) Int. Cl.$^7$ .......................... G01N 1/18; G01N 33/48; B01B 35/00; C12M 3/00; B01F 7/00

(52) U.S. Cl. ....................... 436/177; 210/767; 210/780; 366/213; 366/218; 366/242; 422/99; 422/101; 435/7.21; 435/288.1; 435/288.3; 435/307.1; 435/308.1; 435/309.1; 436/63; 436/179

(58) Field of Search .................... 436/63, 177, 179, 436/810; 422/99, 101; 435/7.21, 288.1, 288.3, 307.1, 308.1, 309.1, 296, 292; 604/317–318, 406; 366/213–214, 218, 242; 210/767, 780, 232, 238

(56) References Cited

U.S. PATENT DOCUMENTS

| | | | | | |
|---|---|---|---|---|---|
| 3,838,809 A | * | 10/1974 | Williams | ...................... | 494/11 |
| 4,430,213 A | * | 2/1984 | Ishikawa | ...................... | 210/136 |
| 4,655,472 A | * | 4/1987 | Pletscher | ...................... | 16/225 |
| 4,845,025 A | | 7/1989 | Lary et al. | | |
| 5,000,922 A | | 3/1991 | Turpen | | |
| 5,016,644 A | * | 5/1991 | Guirguis | ...................... | 600/584 |
| 5,077,012 A | * | 12/1991 | Guirguis | ...................... | 422/58 |
| 5,137,031 A | * | 8/1992 | Guirguis | ...................... | 600/584 |
| 5,139,031 A | * | 8/1992 | Guirguis | ...................... | 600/584 |
| 5,143,627 A | * | 9/1992 | Lapidus et al. | ............. | 210/767 |
| 5,282,978 A | * | 2/1994 | Polk, Jr. et al. | ............ | 210/767 |

(List continued on next page.)

FOREIGN PATENT DOCUMENTS

| | | |
|---|---|---|
| EP | 0 590 504 B1 | 4/1994 |
| WO | WO 94/20385 A1 | 9/1994 |

OTHER PUBLICATIONS

Leonard, E. J. et al, Biotechniques, 1990, 9, 684–9.*

*Primary Examiner*—Arlen Soderquist
(74) *Attorney, Agent, or Firm*—Foley & Lardner LLP

(57) ABSTRACT a method for separating particulate matter from a fluid, using apparatus which includes a container and cover, a filter assembly positioned in a housing atop the cover and suitable for collecting particulate matter in the fluid on a collection surface, and a dispersing element fixed relative to the cover. The cover has a portion that is fixed in a first position and freely rotatable in a second position. The specimen is placed in the container, and a mixer apparatus rotates the container in relation to the cover to disperse the particulate matter throughout the fluid. Upon deactivation of the mixer apparatus, a fluid sample including dispersed particulate matter is drawn through the filter assembly to capture a substantially uniform layer of particulate matter on the collection surface. The housing is then opened to expose the layer of particulate matter, which is then transferred to a microscope slide.

13 Claims, 5 Drawing Sheets

U.S. PATENT DOCUMENTS 5,301,685 A * 4/1994 Guirguis ..................... 600/573
5,422,273 A * 6/1995 Garrison et al. ......... 435/307.1
5,429,803 A * 7/1995 Guirguis ..................... 422/58
5,471,994 A   12/1995 Guirguis
5,624,554 A * 4/1997 Faulkner et al. ............ 210/232
6,296,764 B1 * 10/2001 Guirguis et al. ......... 210/323.1
6,309,362 B1 * 10/2001 Guirguis ..................... 600/573
6,379,565 B1 * 4/2002 Guirguis et al. ............ 210/767
6,423,237 B1 * 7/2002 Guirguis ..................... 210/767

* cited by examiner

METHOD FOR MIXING AND PROCESSING SPECIMEN SAMPLES

This is a national stage application based on International Application No. PCT/US99/15281, filed Jul. 7, 1999, and claims the benefit of U.S. provisional application No. 60/092,029, filed Jul. 7, 1998.

BACKGROUND OF THE INVENTION

1. Field of the Invention

The present invention is directed to an improved apparatus and method for collecting a uniform layer of cells from body fluids suitable for use in improved cytological protocols.

2. Description of the Related Art

In a wide variety of technologies, the ability and/or facility in separating matter, typically particulate matter, from a fluid is a critical component in the ability to test for the presence of substances in the fluid. Too often, interference associated with sample preparation obscures the target cells to such a degree that the process is not sufficiently reliable, or too costly. Reducing interference is frequently a function of adequately separating and dispersing mucoid clumps and cell aggregates.

A similar scenario applies to many other fields which involve detection and/or diagnosis, including environmental testing, radiation research, cancer screening, cytological examination, microbiological testing, and hazardous waste contamination, to name just a few.

All that is required for a cytological examination of a sample is that a sample of cells be obtained from the patient, which can typically be done by scraping or swabbing an area, as in the case of cervical samples, or by collecting body fluids, such as those obtained from the chest cavity, bladder, or spinal canal, or by fine needle aspiration. In a conventional manual cytological examination, the cells in the fluid are then transferred onto a glass slide for viewing. In a conventional automated cytological examination, a filter assembly is placed in the liquid suspension and the filter assembly both disperses the cells and captures the cell on the filter, and the filter is removed and placed in contact with a microscope slide.

In all of these endeavors, a limiting factor in the sample preparation protocol is adequately separating solid matter from its fluid carrier (e.g., a variety of fluids, such as physiological, biological and environmental), and in easily and efficiently collecting and concentrating the solid matter in a form readily accessible to microscopic examination. For some types of biological fluid, particularly sputum, various processing steps for breaking mucoid clumps and breaking cell aggregates are designed to evenly distribute cells in the fluid so that microscopic examination of a portion of the fluid will provide a representative sampling of all of the cells in the particulate matter in the fluid.

The prior art contains a number of methods, apparatuses, and structures for dispersing cells in the fluid. For example, U.S. Pat. No. 5,143,627 opens the sample container, inserts a dispersing element into the liquid suspension, and rotates the dispersing element for several minutes. In another example of the prior art, the Saccomanno method is used to process sputum, a process that is time consuming and involves a large number of processing steps. In U.S. Pat. No. 5,471,994, a syringe is used to draw fluid from a sample container through a filter assembly in a housing attached to the cover of the sample container. Mixing of the fluid to disperse particulate material therein is not addressed in this patent.

Prompt processing of urine to obtain fresh cells traditionally has been recommended to ensure the accuracy of quantitative culture results, urinalysis and microscopy. Fresh cells tend to stick to a glass slide much better than cells from preserved urine, allowing for smoother cell spread onto the glass body. Delays in processing, negligent care in either inpatient or outpatient settings and lack of refrigeration may lead to non-optimal slide preparation. One known solution to the delay problem is the use of chemical preservatives with the urine. The presence of liquid preservatives, however, in the urine specimen raises the specific gravity of the specimen to unmeasurable levels and may limit the potential usefulness of the urine for various types of traditional quantitative analysis, such as slide microscopy.

A number of urine or other biological fluid specimen containers have been developed to allow liquid biological specimens to be tested without removing the lid of the urine or biological fluid container. None of the prior art solves the problem of transferring cells in a uniform layer to a slide for examination while at the same time preserving the fluid from which the cells were taken.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives (e.g., alcohol or acetone fixatives) prior to transferring cells onto the slide or membrane for staining or examination.

Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation. New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifact. These preparations have resulted in an even distribution of cells that have superior morphology, which has improved light microscopic visualization and has allowed for the use of image cytometry instruments.

The solid matter preparation techniques of the present invention address the issues of non-uniform matter densities, uneven matter distribution, and sample loss due to the number of steps involved in the sample preparation. The preparations of the present invention result in an even distribution of solids that have superior morphology, improved visualization, and are readily positioned and available for light absorbency analysis without the need to further manipulate or prepare the sample.

SUMMARY OF THE INVENTION

The present invention relates to use of an apparatus for collecting matter for detection, analysis, quantification, and/or visualization, and is particularly suitable for separating matter from biological, physiological, and environmental fluids and presenting the particulate matter in an improved manner for cytological examination. The present invention is particularly suited to processing sputum or other high mucous content fluids.

The present invention relates to use of an apparatus that includes structures for engaging a portion of the cover of a collection container, and one or more structures for rotating the collection container. The apparatus may be configured to process a single sample container or more than one, and may be operated manually, semi-automatically, or automatically.

In some embodiments of the invention, the cover may include an outer stationary cover and an inner rotatable cover. In a preferred embodiment of the invention, the inner and outer covers are not rotatable with respect to each other in a first position, and are freely rotatable with respect to each other in a second position.

An apparatus used in the present invention includes a structure or element for rotating a sample container and another structure or element for engaging a portion of the sample container, e.g., a portion of the cover, and holding the portion in place.

The present invention relates to use of an apparatus for collecting a uniform layer of cells from urine or other biological fluid specimen in a cytology collection apparatus or assay module, which can be removably detached from a collection container for application to a slide. The patient or medical person handling the collection may seal the separate container. The collection of the cells in the cytology collection apparatus allows a uniform cell slide to be obtained without contamination of the cells by preservatives, workers or outside materials. The transfer from collection container to the cytology collection apparatus may be carried out without pouring or pipetting the collected specimen. Preferably, once the sample has been collected, the devices do not need to be opened in order to separate the particulate matter from the fluid. That is, an apparatus may be a closed system, and particulate matter may be collected using a closed system.

The present invention is directed to use of a cell collection and distribution apparatus that is preferably closed from the time the sample is collected to the time that particulate matter is captured on a collection site. Once the sample is processed, i.e., the sample is collected, particulate matter in the fluid is dispersed, and particulate matter in the fluid is separated from the fluid by collecting it on a collection site, the apparatus is preferably capable of being disassembled to allow face to face transfer of cells from the device to a slide for microscope examination. The present invention provides an improved method for collecting a monolayer of cells that can be transferred to a microscope slide.

The devices involved in the present invention obviate the need for a trained technician to properly prepare a sample substrate. Thus, time, expense, and expertise are eliminated or reduced as critical factors in sample preparation protocols.

The present invention also provides advantages in sample preparation because it is suitable for use with fresh, untreated cells, unmodified cells, and is particularly designed to provide a thin, uniform layer of solid matter (up to approximately 40 microns or more). This invention is particularly useful in gynecological processes, e.g., for collecting cells for a pap smear, and for processing fluids such as sputum that have mucous clumps in the fluid.

The method of the present invention may involve use of a cytology collection and testing kit containing the cytology collection apparatus described above. The cytology collection kit may also include replacement filters, replacement disposables, and/or other components or solutions typically used during cytological examinations.

The present invention has many advantages for conventional microbiology and hematology. The collected cells are in a predetermined area, and for some embodiment of the invention, are easily accessible to a radiant light source and to a wavelength absorbency meter. Because cells are concentrated in a single layer, they are almost always in one focal plane, thus eliminating or reducing interference by other particles and virtually eliminating technician time and expertise-in establishing a proper reading. The minimal matter overlap achieved ensures that all matter can be easily examined with little chance for critical solids to be obscured by clumps of overlapping solids or debris. The involved apparatuses even permit the use of automated devices to detect and analyze any solid matter in a given population. It also permits a detailed analysis of the chemical composition of the matter.

Further, providing a container cover that has a portion that is rotatable permits particulate matter stirring or dispersion without inserting a stirring mechanism into the sample, thus eliminating a source of contamination that plaques devices that are presently commercially available.

The accompanying drawings show illustrative embodiments of the invention from which these and other of the objectives, novel features and advantages will be readily apparent.

DETAILED DESCRIPTION OF THE PREFERRED EMBODIMENT

Figure 1:
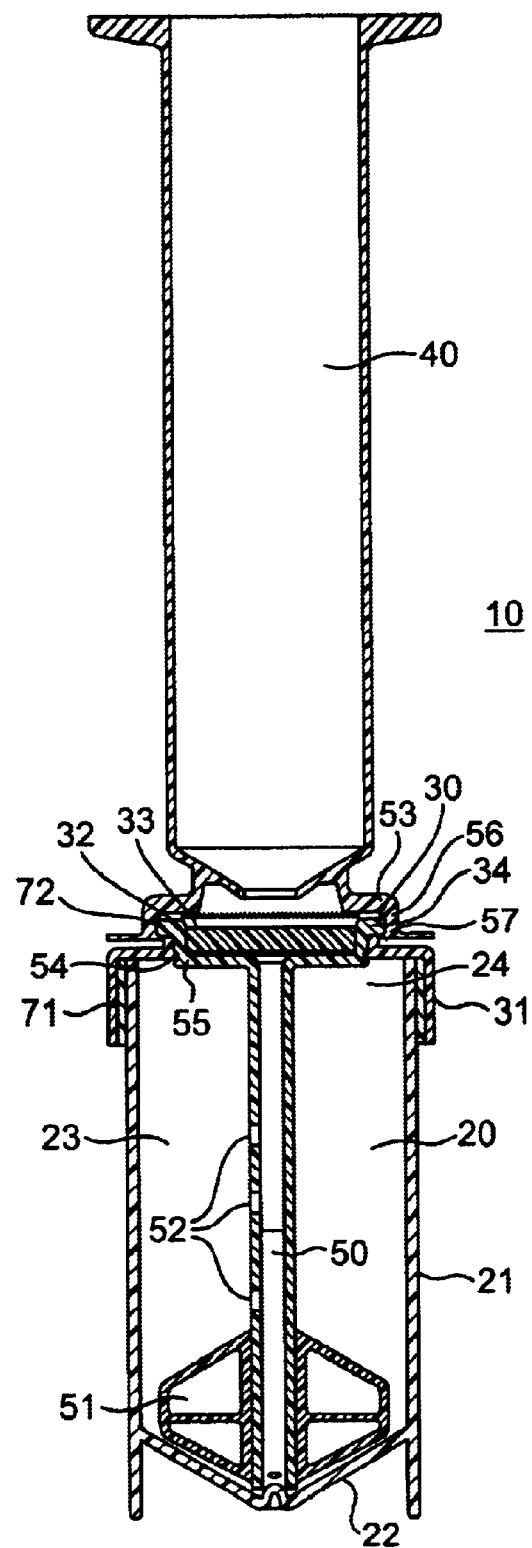
FIG. 1 is a cross section view of an embodiment of the invention.

An apparatus of the present invention includes a container support for positioning and rotating at least one sample container, and a sleeve or clamp for engaging and fixing a portion of the container that communicates with a dispersing element. In a preferred embodiment of the invention, the sleeve engages an inner cover.

An embodiment of the invention includes a sample container having a cover; said cover having a first portion that communicates with a dispersing element, said first portion being matingly engaged to a second portion of the cover, said second portion communicating with the sample container and being rotatable in relation to said first portion; a container support for engaging and rotating the sample container; and a sleeve for engaging and fixing the second portion of the cover.

It is also important to provide structures and means for rotating an agitator in relation to the container and/or the sample in the container. As described in more detail below, an exemplary device according to the present invention may include a cover within a cover, wherein the agitator is fixed to a stationary inner cover and the container and outer cover freely rotate. Such relative motion moves the agitator in relation to the sample, and disperses particulate matter in the fluid.

An instrument according to the present invention preferably employs a fresh sample vial, an unused filter assembly, and an unused microscope slide for each individual cell specimen. Moreover, the relatively simple operation, and the multiple functions that the instrument performs, minimize the requirements for operator attendance and time, as well as minimizing maintenance and preparation. In a preferred embodiment of the invention, the sample container is closed throughout the processing, until particulate matter in the sample is collected on a collection site.

The present invention also includes devices and methods for collecting fluids, such as biological, physiological, or environmental fluids, removing the desired matter from the fluid, without centrifugation, and diagnosing and testing the matter. In a preferred embodiment of the invention, particulate matter is collected on a collection site. In a most preferred embodiment of the invention, the particulate matter is collected in a monolayer and in a pre-determined spatial arrangement.

The present invention also includes an improved apparatus and method for processing a fluid containing particulate matter. The apparatus and method include dispersing particulate matter in the sample, preferably by rotating the sample container around a fixed agitator or the like. The apparatus includes one or more structures for engaging and rotating the sample container and one or more structures for engaging and fixing the portion of the cover of the sample container that communicates with or includes an agitator or dispersing element.

The present invention is also an improved device for collecting a processing a fluid, typically a biological fluid, the device including a particulate matter separation chamber having one or more of the following: a collection site; a membrane for separating particulate matter from a liquid; a porous support; a porous support with at least one throughgoing bore, preferably a bore positioned near the circumference of the porous support, said bore providing additional surface tension so that a filter membrane is retained on the porous support when the housing is opened to expose the membrane for further processing; a porous arrangement that establishes at least two fluid flow paths through the separation chamber; a porous arrangement seat that configures the collected particulate matter in a predetermined pattern; a collection chamber having a concentric channel; a channel having one or more resilient members; a chamber seat having one or more resilient members; a chamber seat or base having posts; a chamber seat having one or more pre-determined surface modifications; a seat having one or more elements that promote a pre-determined spatial arrangement of particulate matter on the collection site; and structures that enhance the fluid flow through the chamber.

A device according to the present invention may also include structures that are configured for and/or are adapted to mix the specimen collected in the collection container. Exemplary structures include but are not limited to a collection container having a rotatable cover, or a portion of the cover that rotates; a cover or cover portion that is moveable in relation to the collection container; and a tube or the like that extends into the collection container, said tube including one or more elements that mix the specimen. The cover may also include a portion that fittingly engages a portion of the cover in a liquid tight seal. The cover may also include a portion that fittingly engages a portion of the cover in a liquid-tight but not fluid-tight seal.

A device according to the invention may also include a pump or syringe portion, said portion optionally including on or more elements configured to permit a pre-determined amount of fluid into the pump or syringe. A device according to the invention may also include structures adapted for communication with a vacuum pump or the like for drawing fluid through the filter assembly.

The devices and methods of the present invention may be configured into a hand-held manual system or structure, a partially automated system or structure, or a fully automated system or structure.

The devices and methods of the present invention represent the first fully closed system for removing particulate matter such as cells from a fluid such as a biological fluid. In accordance with the present invention, once the sample is collected in the sample container and the cover is moved to a first position (described in more detail below), the container or system does not need to be opened until the particulate matter is collected on the collection site and is ready for transfer to a microscope slide.

The present invention also includes preparing a fluid for microscopic examination by processing a fluid using a device according to the invention, and collecting particulate matter on a collection site in the device.

The present invention also includes a method for analyzing matter comprising collecting a sample in a collection container, collecting matter on a collection element, and transferring the matter collected on the collection element to a microscope slide or the like. Preferably, both collecting steps occur within the same housing.

A device according to the invention may also include one or more separable elements. In a preferred embodiment of the invention, the device includes a separable porous arrangement housing. In a most preferred embodiment of the invention, the device includes a porous arrangement housing having a top portion of the housing configured to retain at least a portion of the porous arrangement.

The present invention also includes a kit having an assay module, which includes a matter collection element according to the invention, a fluid specimen container, and a pump for inducing fluid flow through the assay module.

In a preferred embodiment of the invention, a specimen container includes a chamber for collecting a liquid specimen, and in fluid communication with the chamber, a particulate matter separation chamber or module for separating particulate matter in the fluid and collecting the separated particulate matter in a collection zone. In a most preferred embodiment of the invention, the separated particulate matter is collected in a monolayer on the collection zone. A preferred embodiment of the invention also includes a hollow tube in fluid communication with the particulate matter separation chamber. More preferably, the hollow tube includes means for mixing the specimen and/or dispersing the particulate matter in the specimen. Exemplary means include but are not limited to an agitator, fins, brush, swab, broom, spatula, or the like.

In another embodiment of the invention, the apparatus includes the specimen container and particulate matter separation chamber described above, and a pump or syringe or the like. In this embodiment of the invention, the various structures provide a fluid flow path from the specimen container, through the particulate matter separation chamber, and into the syringe.

As used herein, "sample" refers to any fluid in combination with solid matter, such as particulate matter, and from which it may be desirable to collect the particulate component from the sample for the purpose of establishing its identity or presence in the sample. Typically, the fluid component of the sample will be a liquid. However, the fluid may also be air or gas. As an example, it may be desirable to determine the presence of cancer cells or certain proteins in the biological fluid, such as urine. In another example, it may be desirable to evaluate the nature of contaminants, such as molecular contaminants, in ultra-pure water used in the electronics industry. Other exemplary fluids include but are not limited to body fluids, such as blood, spinal fluid, or amniotic fluid; bronchial lavage; sputum; fine needle aspirates; ground water; industrial processing fluids; and electronic or medical dialysis fluids, to identify just a few. It is intended that the invention should not be limited by the type of fluid being processed.

As used herein, "particulate matter" refers to any substance in a fluid that is capable of collection and evaluation, preferably by cytological examination. Exemplary particulate matter includes, but is not limited to cells or cell fragments, proteins, molecules, polymers, rubbers, stabilizers, antioxidants, accelerators, silicones, alkyds, thiokols, paraffins, thermoplastics, bacteria, pesticides, and herbicides. Specific exemplary polymeric matter include, but is not limited to polyethylene, polypropylene, polyisobutylene, polyacrylonitrile, polyethylene glycol, polyvinylchloride, polystyrene, polysulfide, polymethylmethacrylates, polyethyleneterephthalates, bisphenol A (a common environmental contaminant), ethyl cellulose, nitrocellulose, polyurethane, and nylon. Specific exemplary biological matter includes cancer cells, including distinguishing between metastatic and normal cancer cells; proteins, nucleic acids, antibodies, or the like. It is intended that the invention should not be limited by the type of matter being processed.

While a cytology collection apparatus according to the invention can be used for any biological fluid, it is particularly useful,for preparing testing samples from urine and its associated cells for Pap smears, or for sputum. The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatic patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is very pleasing to the eye, possibly reducing eyestrain.

It is intended that the invention should not be limited by the type of matter being processed. In a most preferred embodiment of the invention, the fluid is urine and particulate matter is a cell.

The particulate matter processing apparatus of the present invention also permits isolation and collection of fresh cells and/or microorganisms from biological fluids to perform DNA probe and chromosomal analysis once the cells are hemolyzed by the proper buffer.

As used herein, "adapted for communication," "communicating," or similar terms refer to any means, structures, or methods for establishing fluid flow through the system, as are well known by practitioners in the art. Exemplary structures are shown in the Figures. For example, a conduit may have a connector adapted to receive or connect to a mated connector on another conduit. As used herein, connector refers to any structure used to form a joint or to join itself to another piece. These connectors or connections establish a fluid flow path through various elements of the apparatus, assembly, or system. Typical connections include but are not limited to mating connections, such as Luer-type, screw-type, friction-type, or connectors that are bonded together.

As used herein, "adapted for engaging," "engagement," "engaging," or similar terms refers to complementary structures that may align, mesh, mate or rest near, against, or within each other. Exemplary structures include the connectors described above.

In a most preferred embodiment of the invention, the specimen or sample is collected in a sample container having the design and function as described below. The sample container is typically covered, and has a portion that may be suitable for engaging a filter assembly. In preferred embodiments of the invention, the container or cover includes a central recessed portion adapted to receive the filter assembly. In some embodiments of the invention, the central recessed portion also communicates with or engages a hollow tube that extends into the specimen container. Optionally, a portion of the tube may include a stirring, dispersing element, or agitator.

Figure 3:
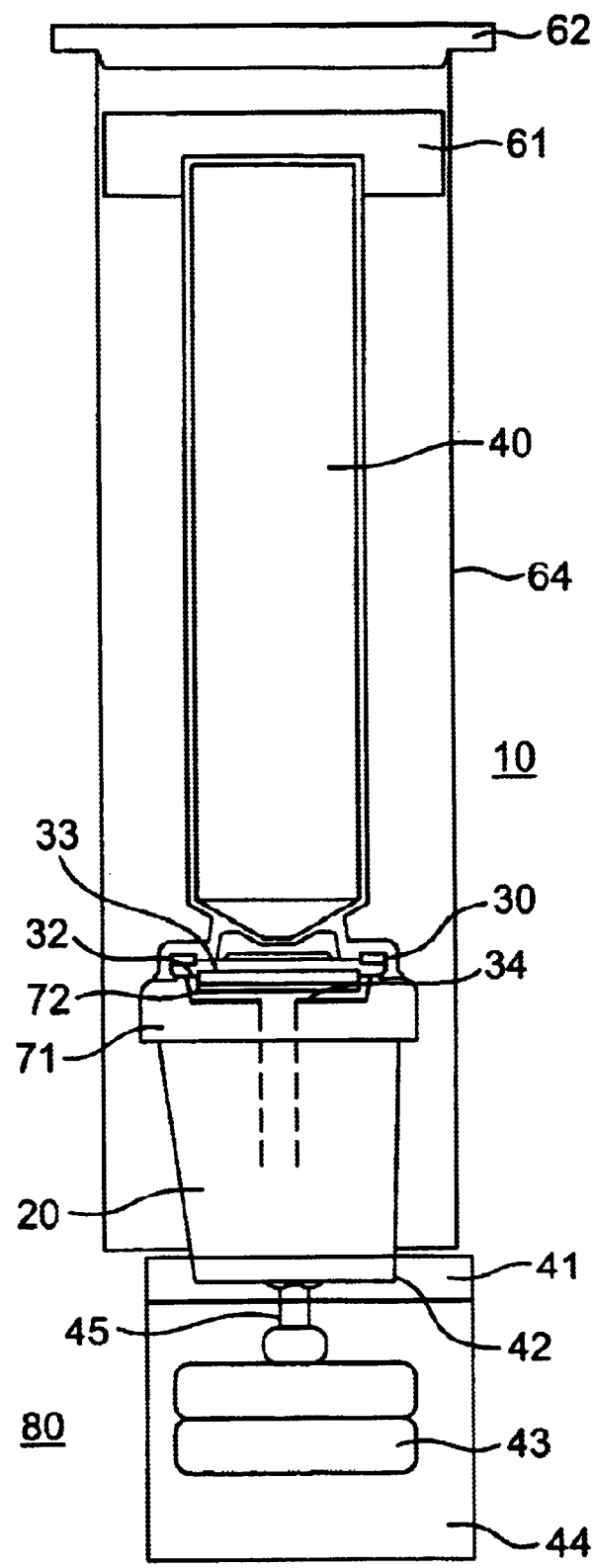
FIG. 3 is a cross section of a mixer according to the invention.

The present invention, an exemplary embodiment of which is shown in FIG. 1, includes a particulate matter separation device 10 including a specimen collection container 20 defining a collection chamber 23, a particulate matter separation housing 30 defining a housing for a porous arrangement 33, and a pump 40 in the form of a syringe. FIG. 1 also shows hollow tube 50 in the embodiment of the invention that includes an agitator 51. FIG. 3 shows the complete mixing assembly comprising mixer 80 having a rotatable container support in the form of a platform 41 adapted to receive a bottom portion of container 20. Container 20 includes a cover, preferably having a first portion 71 that is rotatable with container 20 and a second portion 72 that is fixed. Second portion 72 of the cover includes or engages or communicates with a tube 50 that extends into container 20, and includes a lower portion 32 of the porous arrangement housing. As illustrated, second portion 72 is integrally configured with or adapted to engage an end portion of a pump 40. The apparatus according to the invention also includes a sleeve 64 or the like adapted to cover the syringe-container assembly, preferably maintain the alignment of the container and the syringe on the container support. Sleeve 64 preferably includes a gasket 61 or the like for engaging and positioning the pump 40 within the sleeve. Optionally, sleeve 64 may include a cover 62. In a preferred embodiment, the gasket in the sleeve matingly engages a portion of the cover.

In accordance with an alternative embodiment of the invention, the specimen collection and processing assembly 10 may be adapted for use with multiple containers multiple container supports, and multiple sleeves, or a single sleeve having multiple gaskets.

In preferred embodiments of the invention, a specimen container includes a chamber for collecting a liquid specimen and a cover that establishes fluid communication between the chamber and a filter assembly for separating particulate matter from the fluid and collecting the particulate matter at a collection site. In most preferred embodiments of the invention, the separated particulate matter is collected in a monolayer on a membrane according to the invention. Preferred embodiments of the invention also include a cover having a hollow tube establishing fluid communication between the sample and the filter assembly.

More preferably, the hollow tube includes means for mixing the specimen and/or dispersing the particulate matter in the specimen.

Each of these elements will now be described in more detail.

In accordance with the invention, the container support is rotatable around an axis. Bearings may be provided that facilitate movement of the support, and may be rotatable by a transmission such as a belt drive, gears, or the like; and movable vertically using a stepper or the like.

Platform 41 preferably has one, and optionally a plurality of, sockets 42 adapted to receive a bottom portion of specimen container 20. Specimen container 20 may fit snugly in socket 42, or socket 42 may include any of a variety of resilient members that position and hold the specimen container in place. An exemplary resilient member includes an O-ring or a rubber gasket.

A specimen container may be positioned by hand or mechanically on a container support for further processing in an apparatus according to the invention. The container support is preferably a substantially planar platform, disc, sheet, shelf, tray, or the like. In preferred embodiments of the invention, a sample container includes guides suitable for positioning and/or retaining one or more specimen containers. In more preferred embodiments of the invention, the container support includes one or more recesses or cavities adapted to accommodate at least one size of sample container. In a most preferred embodiment of the invention, the container support includes at least two recesses for accommodating at least two different size sample containers. The container support is preferably movable, i.e., adapted to rotate around an axis, thereby rotating the specimen container.

As shown in FIG. 3, platform 41 rests on or forms a portion of housing 44. Housing 44 encloses a centrally located drive, sun gear, motor 43, or the like. Motor 43 may be adapted to engage a plurality of planet gears adapted to communicate with or corresponding to socket 42 or container 20. A portion of the socket may include a gear or teeth adapted to engage a belt or the like so that the platform 41 is rotatable. As noted above, this belt driven rotational movement is transferred to the specimen container so that agitators extending into the container stir the sample.

In a preferred embodiment of the invention, rotational movement of the connecting rod 45 turns the socket 42, which in turn rotates container 20 in relation to fin 53. Alternatively, connecting rod 45 may include an element that engages and rotates fin 53.

In accordance with the invention, specimen container 20 includes any container suitable for holding a fluid, preferably a biological fluid. The typical container includes sidewalls 21 and bottom wall 22 that, in combination, provide a chamber 23 having an open end 24 for collecting, holding, or storing a fluid. Typical fluids include, but are not limited to biological fluids, such as body fluids, wastewater fluids, or the like. Typical body fluids include urine or other biological fluids, such as blood, cerebrospinal fluid (CSF), bronchial lavage, sputum or fine needle aspirates.

The configuration and materials used to make the container (and any of the elements that comprise a device according to the invention) can be any of a variety of materials, shapes, and sizes. For example, the container can be constructed of any material compatible with the fluid to be processed. It will be appreciated that the container and the assembly of the sidewalls to the bottom wall can be any conventional assembly. In a preferred embodiment of the invention, bottom wall 22 is a conical member, as shown in FIG. 1. Optionally, bottom wall 22 or sidewall 21 may include one or more fins or the like (not shown) extending into the chamber. Such fins may be desirable an embodiment of the invention described in more detail below in which the sample in the container is mixed by rotation of the container.

Figure 2:
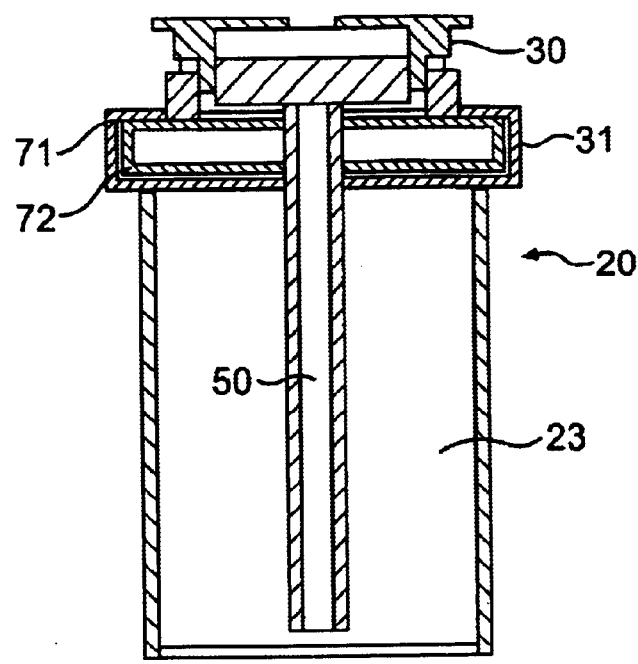
FIG. 2 is a cross section view of the container cover of an embodiment of the invention.

As shown in FIGS. 1–3, a device according to the invention also includes a cover or lid 31. In a preferred embodiment of the invention, the cover is configured or adapted to receive a lower portion 32 of a porous arrangement housing. The cover 31 may include a downwardly extending member 71 configured to engage sidewall 21 of container 20. It is intended that cover 31 may be any configuration or shape that closes or seals open end 24 of container 20.

The cover also includes a top portion 53 having an opening adapted to receive the lower portion 32 of the porous arrangement housing. Although the engagement between top portion 53 and lower portion 32 may be variously configured, lower portion 32 preferably includes a groove 55 adapted to receive a projection 54 in top portion 53. In a most preferred embodiment of the invention, the engagement is a snap fit, with the engagement between porous arrangement housing portion 32 and the projection 54 permitting housing portion 32 to rotate. This configuration is preferably liquid tight, and in a most preferred embodiment of the invention, the seal is liquid tight but not fluid (e.g., air) tight.

An alternative configuration for the cover 31 is shown in FIG. 2. The cover may be variously configured to achieve the desired function. In this embodiment of the invention, cover 31 includes structures and means for allowing an outer portion of the cover to move in relation to an inner portion. As illustrated, cover 31 includes outer cover 71 and inner cover 72. Inner cover 72 is preferably fixed to or in fluid communication with tube 50. In a preferred embodiment of the invention, cover 71, when tightened to container 23 rotates about inner cover 72 and tube 50. Such relative motion between outer cover 71 and inner cover 72 moves sample in the container 23 in relation to agitator 51.

The most preferred embodiments of the invention include a cover having an inner portion or cover and an outer portion or cover, and wherein closing the cover and releasing one of the covers or portions so that it is freely rotatable occurs in a multi-step procedure. When the inner and outer covers are used to seal the container, it is preferred that the inner and outer covers do not freely rotate in relation to each other. Both covers seal the container up to a first position. In a second position, a catch or seal or the like is broken, e.g., by an additional twist of the outer cover, thus freeing the outer cover from its connection with the inner cover. In the second position, the outer cover rotates freely in relation to the inner cover.

Figure 5:
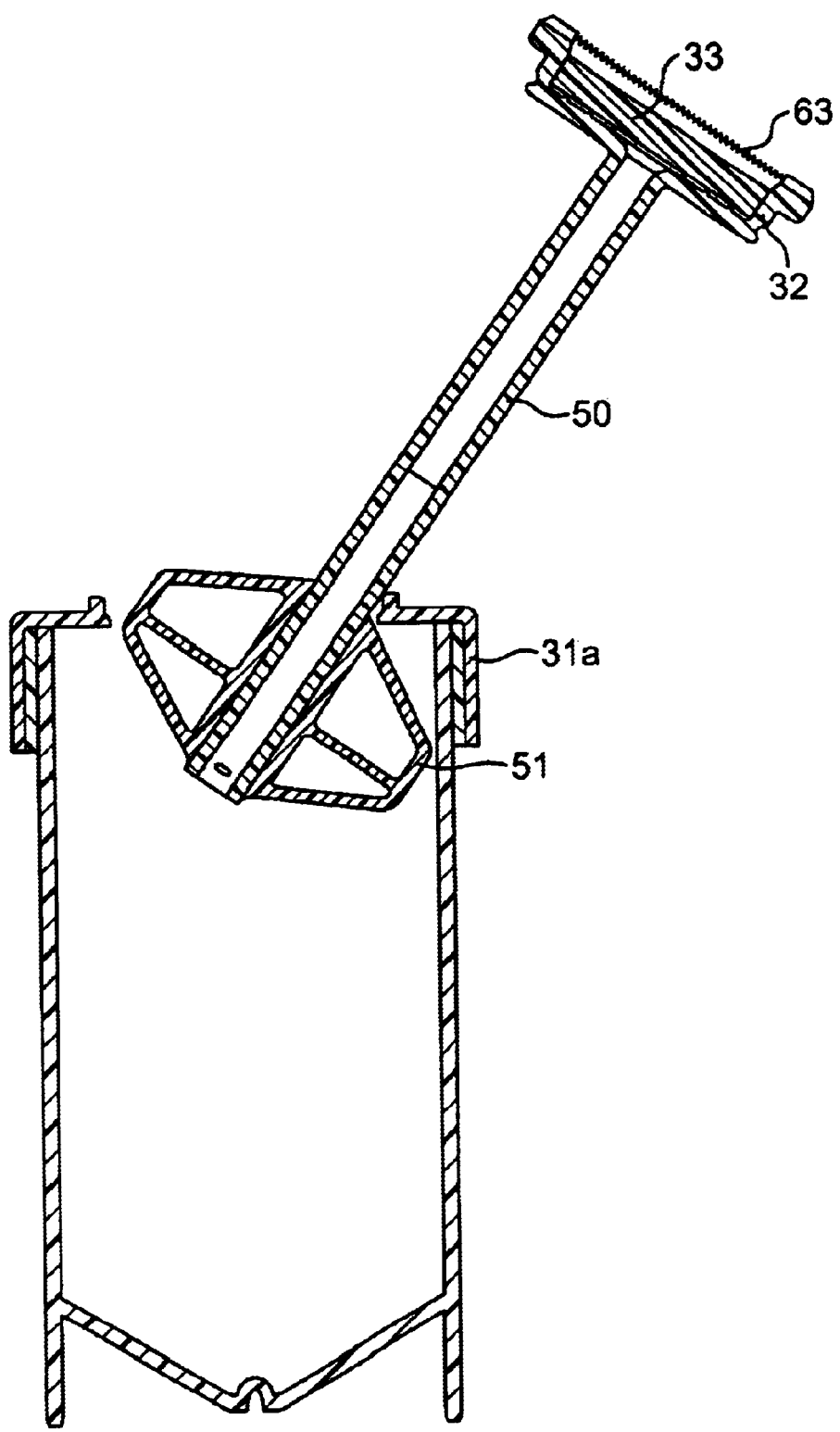
FIG. 5 is a cross section view of a disassembled base, hollow tube, and container.

FIG. 5 also illustrates another embodiment of the invention relating to a cover having a slot through which the agitator or brush can be positioned inside the container. In a preferred embodiment of the invention, the slot or opening in the cover can be covered with a removable or penetrable covering that protects the inside of the container from contamination until the container is ready for use. For example, a brush or the like can be used to collect a cervical sample, the covering can be removed from the cover, and the brush can be placed in the container.

In accordance with the present invention, a device according to the invention includes a particulate matter separation housing that may be variously configured. Any housing 30 adapted to receive a porous arrangement 33 may be used.

As shown in FIG. 1 the particulate matter separation housing 30 is preferably a two piece housing formed by a top portion 53 and lower portion 32. In a preferred embodiment of the invention, top portion 53 releasably engages lower portion 32; any housing configuration or assembly providing access to the porous arrangement 33 is suitable. Top portion 53 and lower portion 32 may be connected or fastened to each other by any mating connection or means that provides a liquid or fluid tight fit, e.g., Luer-type (threaded or not threaded), screw thread-type, friction-type, a tapered mating connection, or snap fit (as illustrated).

Figure 4:
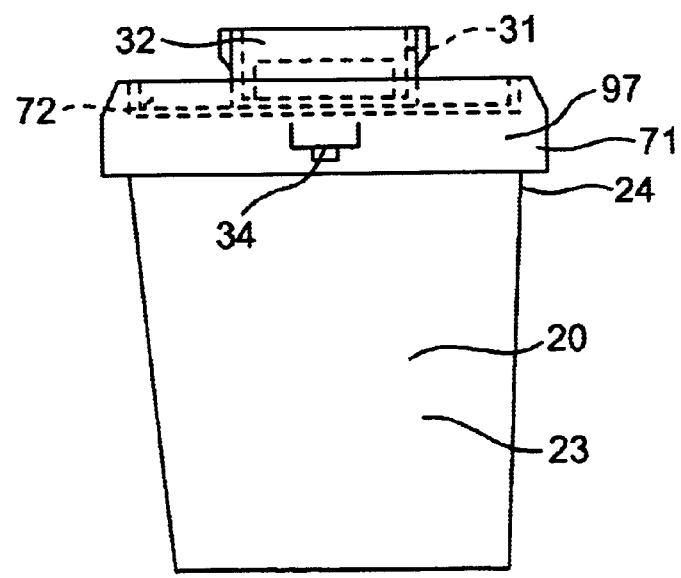
FIG. 4 is a cross section of a specimen container and alternative cover according to the invention.

Lower portion 32 includes a side wall and bottom wall suitable for seating a porous arrangement 33. Lower portion 32 may also include a central bore or aperture 34 communicating with a hollow tube 50. In a preferred embodiment of the invention, hollow tube 50 extends into specimen container 20. In a preferred embodiment of the invention, lower portion 32 may be a separate structure that is capable of rotating in the base 31a. In order to achieve ease of centrifugal rotation while maintaining a liquid-tight assembly, lower portion 32 may matingly engage base 31a through a tongue and groove arrangement (see FIGS. 1 and 3). Alternatively, the cover may include an inner cover and an outer cover (FIGS. 2 and 4), or portions that are moveable in relation to each other.

Figure 6:
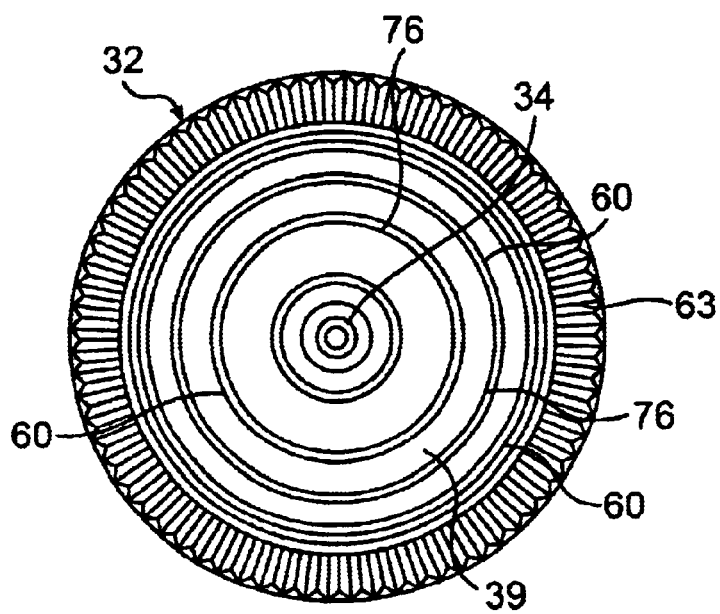
FIG. 6 is a top view of filter assembly housing seat, and in some embodiments, a top view of the top of the inner cover.

In accordance with an embodiment of the invention, lower portion 32 of the porous arrangement housing includes a bottom wall or seat 39. As shown in FIG. 6 seat 39 may include one or more spaced apart ribs or projections 60. Projections 60 are preferably of a configuration, size, and shape sufficient to prevent porous arrangement 33 from flush contact with seat 39. In the embodiment shown in FIG. 6, projections 60 are concentric rings.

Alternative configurations are described in more detail below. In a preferred embodiment of the invention, projections 60 function in one or more of the following ways: projections 60 may break the surface tension between porous arrangement 33 and seat 39 so that, during use, when porous arrangement 33 is pulled away from seat 39, first porous medium 36 does not remain in contact with seat 39; projections 60 may evenly distribute pressure of the porous arrangement in the housing; projections 60 may prevent or suppress compression of the porous arrangement; and projections 60 may be configured to distribute any collected particulate matter in a pre-determined configuration or spatial distribution.

In accordance with the present invention, the surface of seat 39 may include one or more structures, configurations, or surface textures that promote the ability of the porous arrangement to release from the seat, that promote a predetermined spatial distribution of particulate matter on the collection site, and/or prevent or suppress compression of the porous arrangement. One embodiment of the invention includes concentric projections, such as projections 60 described above. In a most preferred embodiment of the invention, the surface of the seat is configured into a sundial or clock face structure. Both of these embodiments, as well as other surface configurations disclosed herein, promote the collection of particulate matter on the collection site in a predetermined spatial arrangement. Other configurations include, but are not limited to a grid, cross-hatching or the like, concentric squares or rectangles, or a series of continuous or separated structures, nubs, protuberances, granulations, or the like. It is intended that any element, structure, or chemistry that provides a texture to the surface of the seat is suitable for use with the present invention.

In accordance with another embodiment of the invention, the seat 39 and/or lower portion 32 may optionally include a channel or the like. In a preferred embodiment of the invention, seat 39 slopes slightly outward toward the channel. The slight slope of the seat and the channel promote enhanced fluid flow through the housing and decreases the surface tension of the seat, both of which promote the capability of the porous arrangement to disengage from the lower portion 32 of the porous arrangement housing. This aspect of the invention is another structure(s) that promote release of the porous arrangement.

In accordance with the invention, the particulate matter separation chamber 30 is configured to receive a porous arrangement 33 having a particulate matter collection site on the first porous medium 36 adapted to collect particulate matter as fluid containing the particulate matter passes through the housing 30.

Figure 7:
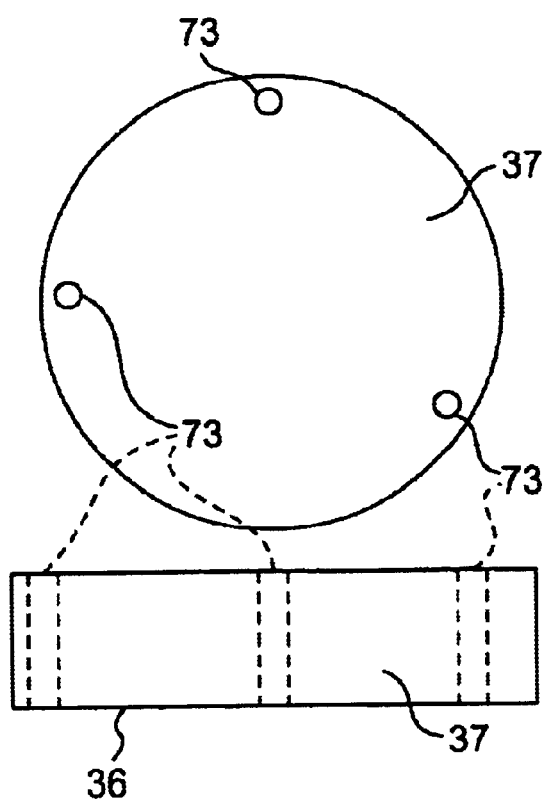
FIG. 7 is a top and cross section view of an alternative porous arrangement according to the invention.

As shown in FIG. 7, to insure that the first porous medium 36, e.g., a filter membrane, is retained on second porous medium 37, one or more through-going bores 73 may positioned in the second porous medium 37.

Porous arrangement 33 having a collection site on the first porous medium 36 adapted to collect matter may be positioned across a fluid flow path, the collection site communicating with hollow tube 50. The porous arrangement 33 within the matter separation chamber is preferably adapted to define at least one fluid flow path having first and second branches, the first branch extending through the collection site and the second branch bypassing the collection site.

The nature of the material used to make the porous media, the compatibility of the materials chosen for the porous media with one another and with the liquid to be processed are all factors to be considered in selecting a particular material for a porous medium for a given application.

In a preferred embodiment, the invention includes a porous arrangement 33 having a first porous medium 36, suitable for preventing the passage of matter therethrough, and a second porous medium 37, suitable for allowing fluid to pass therethrough. The second porous medium may or may not be capable of removing particulate matter from the fluid, a design choice according to the needs of a particular device. In a preferred embodiment, the first porous medium is suitable for capturing or collecting particulate matter, and even more preferably, capturing or collecting solid matter in a uniform or single layer. A preferred embodiment also includes a second porous medium that is suitable as a support for the first porous medium.

In a preferred embodiment, the porous arrangement includes a first porous medium comprising a porous polycarbonate membrane, suitable for preventing the passage of cells therethrough. The porous arrangement may further include second porous medium comprising a depth filter. The depth filter may be made of polypropylene or high-density polyethylene POREX® porous plastics. It is intended that surrounding portion 63 is a structure and configuration that reduces or ameliorates compression of the porous arrangement when it is positioned in the porous arrangement housing.

It should be noted that various types of porous arrangements can be used interchangeably with that of the present embodiment. While a polycarbonate membrane is especially suitable for use in the cytology collection apparatus of the present invention, other porous membranes are also suitable. Exemplary porous membranes are well known in the art, and are disclosed in U.S. Pat. Nos. 5,471,994 and 5,301,685.

The porous membrane preferably has a pore size from about 0.22 microns to about 8 microns, more preferably from about 1 micron to about 6 microns, most preferably about 2 microns, which allows it to trap cells which are more than 3 microns in size. The membrane, is suitable to allow fluid flow to pass therethrough while preventing the passage of particulate matter. The second porous medium is suitable for passing fluid therethrough and may also be capable of removing particulate matter from the fluid. The pore size of the second porous medium may range from about 5 microns to about 60 microns, preferably from about 15 microns to about 45 microns, most preferably about 35 microns.

As one skilled in the art will recognize, adjusting the pore size of the porous membrane and the porous depth fitter in accordance with the type and/or size of matter to be collected permits the collection of the matter on the collection site 14. In a preferred embodiment of the invention, the pore size is chosen so that a uniform layer of matter, preferably a monolayer of matter, is formed on the collection site. For example, from about 3 $\mu$m to about 40 $\mu$m or more has been shown to be effective, but it is intended that the invention should not be limited to a certain range of pore size.

In another embodiment of the invention, well 32, tube 50, and fins 51 form an integral unit, and may be separated from base 31 a to facilitate removal of the integral structure from container 20. An exemplary structure of this embodiment of the invention is shown in FIG. 5.

In accordance with the invention, specimen container 10 includes a pump 40. In a preferred embodiment of the invention, pump 40 is a syringe or the like for altering differential pressure within the apparatus so that fluid can move through the specimen container.

In accordance with the present invention, the pump may be variously configured. In a preferred embodiment of the invention, pump 40 includes an end that forms the top portion 53 of the porous arrangement housing. Top portion 53 includes a seat or the like configured to engage a downstream portion of porous arrangement 33. In a preferred embodiment of the invention, the seat positions porous arrangement 33 in the housing so that porous arrangement 33 does not move during use. In a most preferred embodiment of the invention, the seat includes a plurality of projections or posts of a size, shape, and number to position the porous arrangement in the particulate matter separation housing 30, to promote substantially even distribution of pressure against the porous arrangement, and to reduce or prevent compression of the porous arrangement that interferes with fluid flow through the porous arrangement.

In a preferred embodiment of the invention, top portion 53 removably engages bottom portion 32 to form a porous arrangement housing. Top portion 53 may engage bottom portion 32 in any manner and with any structures that allow top portion 53 to disengage bottom portion 32. In a preferred embodiment of the invention, illustrated in FIG. 1, top portion 53 includes a downwardly extending side wall 56 having a flange 57 or the like adapted to releasably and/or resiliently engage a shoulder 46 or the like on bottom portion 32.

Any suitable pump type device, such as an autovial spunglass filter manufactured by Genex Corporation, could be used. Also included in the scope of the present invention is the use of a flexible, collapsible container, such as a specimen container, which may be squeezed to force fluid through the cytology collection apparatus and into the syringe.

Movement of a fluid through the system may be effected by maintaining a pressure differential between a source of fluid and a destination of the fluid. Exemplary means of establishing this pressure differential may be by applying pressure to any part of the system on the inlet side of the housing (e.g., the collection container); applying a vacuum to any part of the system on the outlet side of the housing (e.g., the syringe); or any form of pump, such as an autovial spunglass filter (manufactured by Genex Corporation); gravity head; or a flexible, collapsible container, such as a specimen container, which may be squeezed to force fluid through the matter collection apparatus and into the syringe. In a preferred embodiment of the invention, a syringe draws fluid from a collection container through the housing.

In accordance with a preferred embodiment of the present invention, specimen container 10 includes a tube 50 or the like for drawing fluid from the collection chamber 23 into the particulate matter separation chamber 30. Typically, tube 50 will be hollow and open or openable at both ends. Tube 50 includes open end 52a near the bottom of the collection chamber 23, and may include one or more apertures 52 into tube 50. Open end 52a and/or apertures 52 permit different fluid layers as well as sediments to be simultaneously tested when the fluid is withdrawn from the collection chamber. In preferred embodiments of the invention, the connection between the tube and the inner cover may be sealed with a washer, gasket, or the like to seal the connection. Alternatively, the seal may comprise a tube-sealing diaphragm that closes around the tube.

In accordance with another embodiment of the improved invention, hollow tube 50 includes at least one agitator projection or fin 51 or the like, as shown in FIG. 1. In a preferred embodiment of the invention, hollow tube 50 is rotatable and agitator fin 51 stirs the liquid specimen, and in a most preferred embodiment, disperse cells and/or particulate matter, and/or to disrupt any large particulate matter such as mucoid bodies. The agitator may also include a body that is independent of the tube 50, and that is induced by a magnetic or electric field to stir the sample.

In an alternative embodiment of the invention, the agitator may comprise fibers, a brush, swab, or broom or the like. Preferably, such fibers or brush is are suitable for dispersing particulate matter in the container when the sample is vortexed in relation to the agitator, brush, or broom. In a most preferred embodiment of the invention, the brush or broom is also suitable for use in collecting particulate matter from a patient, e.g., a cervical brush or broom or the like. It is intended that the brush can be fixed to a portion of the cover, or the cover may include a slot or the like for matingly engaging a portion of the handle on the other end of the brush.

In a most preferred embodiment of the invention, hollow tube 50 and lower portion 32 are of unitary construction, and the lower portion 32, tube 50, and fin 51 are stationary in relation to the rotatable specimen container 20. For example, if the container is rotated, optional fins in the side and/or bottom walls of the container may create concentric movement of the sample in the container, movement that will be disrupted by the presence of fin 51. Alternatively, lower portion 32, tube 50, and fin 51 may be rotated within a 25 stationary container.

A mixer according to preferred embodiments of the invention may include an agitator for stirring each sample in its respective specimen container. As noted above, each head may include a portion that engages a stirring element extending into the sample. This portion of each head is adapted to be connected to a movement transmission, e.g. a motor rotating a belt, or the like that will rotate the portion of each head. The movement transmission may engage a single head, or preferably, engage all of the heads. The belt of a movement transmission may alternatively be activated by rotation of the specimen container supports around an axis.

One skilled in the art will readily recognize that the rotation speed and duration affect the amount of dispersion and the adequacy of breaking clumps or mucoid bodies in the sample. It is well known that the higher the rotation speed, the lower the duration. Using the device and fixative solution described herein, the inventors have found that using high-speed rotation provides optimum cellular distribution in the sample. According to a preferred embodiment of the present invention, the rotation speed should be between 2,000 rpm and 10,000 rpm, and the duration may be as little as one minute. In a most preferred embodiment, for samples having highly mucoid bodies, such as sputum, the rotation speed is about 3,000 rpm and the duration is about 5 minutes. Of course, samples having bodies that are more readily dispersed may require less duration for a given rotation speed.

The present invention is also directed to a particulate matter collection and testing kit containing the collection apparatus 10 as an integral unit. As noted in more detail below, a kit may a include at least one specimen container, at least one particulate matter separation assembly, at least one pump, and at least one porous arrangement. A kit according to the invention may also include replacement filters, replacement disposables, and/or other components or solutions typically used during particulate matter testing or examination procedures, e.g., cytological examinations. For example, a kit might also include washing, fixative, and/or buffer solutions. A cervical kit may include a brush or broom, and a fluid suitable for storing the used brush until particulate matter on the brush can be processed through the filter assembly.

In accordance with preferred embodiments of the invention, the apparatus may include one or more controllers for selectively moving and positioning an element of the automated apparatus, for initiating or discontinuing an operation of the apparatus, or for monitoring the progress of the operation of the apparatus. An example of a preferred controller is a computer and computer program. Other uses of a controller will be evident to one skilled in the art, and are included within the invention.

An apparatus according to the invention may also include a variety of movement transmissions including belts, motors, pulleys, anti-friction elements, lifters, transports, and supports, as well as conduits, a rinsing or cleaning head and its source or supply (e.g., container) of a rinsing or cleaning solution, a fixative applicator and its source or supply (e.g., container) of fixative solution, and the like to effect operation of the elements of the apparatus. Other additional or substituted structures will be evident to one skilled in the art, and are included within the invention.

It will be clear from the description of the various elements of the apparatus that a wide variety of methods of operation may be used. An exemplary mode of operation is described below, and it is intended that the nature, sequence, and number of steps are exemplary.

A group of specimen containers containing respective samples are arranged on a container support, either manually or by a loader. In some embodiments of the invention, a technician enters into the controller one or more of the following parameters for each specimen container: specimen type (e.g., sputum, blood, urine, spinal fluid, etc.) mixing rate, mixing time, suction level, suction time, fixative (e.g., either a yes or no value), and drying time. After the appropriate parameters are loaded into the apparatus, the apparatus initiates sample processing. In preferred embodiments of the present invention, a bar code reader detects a bar code on each container, and the controller selects appropriate parameters based on bar coding on each container.

In operation, a technician places or collects a liquid sample in container 20 and closes the container with a cover 31/pump 40 assembly. A bottom portion of container 20 is then positioned in socket 42. The technician may then activate a motor or the like that rotates a sun gear, which in turn rotates planet gears, which in turn rotate container 20 around an axis. When mixing is complete, the plunger is drawn out of the pump body. Movement of the plunger draws sample in the container 20 through the particulate matter separation housing and through the porous arrangement and into the chamber in pump 40. Each of these steps may be repeated as often as desirable.

The present invention also includes a the method for removing particulate matter from a fluid, and for transferring particulate matter, such as cells, to a microscope slide. In contrast to currently available methods, the use of membrane filtration provides a method of depositing cells evenly over a microscope slide with minimal overlap. This allows for clear observation and optimal diagnostic accuracy.

A method includes collecting a fluid sample containing particulate matter in a collection container 20. The container 20 is then capped with an assembly that includes one or more of the following: base 31a, particulate matter separation chamber 30, and pump 40. Pump 40 is then activated to pull fluid from container 20 through particulate matter separation chamber 30 into pump 40, e.g., by withdrawing the piston in a syringe.

In the embodiment of the invention that includes an inner and outer cover, it is preferred that the inner and outer covers are adapted to engage each other so that the respective covers do not rotate until the final closing of the cover on the container. It is intended that at least initially, the respective covers act as a unitary cover. When the cover is tightened to a pre-determined position, however, it is intended that any structures holding inner cover in place in relation to the outer cover be broken or released so that inner and outer covers rotate freely with respect to one another. Such configurations are well known in the art, e.g., a cover that opens to a first partially open position, then with extra pressure, the cover can be moved to a second or completely free position.

When the fluid is pulled from the collection container 20 to the pump, fluid will flow through porous arrangement 33 so that a monolayer of particulate matter is formed on collection site 36. Once the monolayer of cells is formed, fluid flow is reduced in the center of porous arrangement 33 and increases towards the edges of the porous arrangement. This may be due to the blockage of fluid flow by the collected cells as they form the monolayer on the surface of the porous arrangement. When the monolayer has mostly covered the surface of the porous arrangement, the flow of fluid bypasses the first porous medium and passes through the extended side area of the second porous medium. Thus, the area of the second porous medium extending beyond an end wall of skirt of the top portion acts as a vent (with low resistance to flow) which prevents cells piling up or collecting in more than a monolayer. Fluid may be passed back and forth through the porous arrangement as many times as desirable.

Pump 40 may then be disconnected from base 31a, and thereby exposing porous arrangement 33. Once porous arrangement 33 is removed from well 32, easy access is gained to first porous medium 36. Alternatively, removing top portion 53 from pump 40 may include removing porous arrangement 33 from well 32.

The first porous medium may then be pressed against a microscope slide to allowing particulate matter collection on the collection site to be transferred as they were collected onto the slide. This allows a cytological examination to be performed on the cells by the practitioner without the interference of the pores in the membrane or delay due to processing requirements.

Since cellular detail is dependent on fixation, it is preferred that cells be fixed immediately after being deposited on the slide. Too long a delay between preparation and fixation may expose the cells to drying, which may be detrimental to the cellular structure. Moreover, air-drying artifacts can adversely affect the subsequent staining results. An exception is when the cells are stained with Wright-Giemsa, where air-drying is used as the fixation step.

In an another embodiment of the present invention, the monolayer of cells may be fixed directly on the collection site. This may be carried out by first depositing a monolayer of cells on the collection site of the cytology collection apparatus as described above and subsequently passing a solution containing a fixative, such as alcohol or acetone, through the cytology collection apparatus.

A process according to the present invention may include one or more of the following steps:

1. Provide to a patient a specimen container and a cover. The cover can be a shipping cover, a cover that seals the container but does not include any rotatable portion, or a cover having a first rotatable portion and a second portion, as described above;
2. The patient places the sample in the specimen container, and if a shipping cover is provided, closes the cover. If a two-part cover as described herein is provided, the cover is closed to a first position.
3. The sealed sample container is then delivered to the laboratory.
4. If the sample container includes a shipping cover, the cover is removed by a technician and replaced with a cover having a rotatable portion and a stationary portion. If the sample container includes a two-part cover, the technician moves the outer cover to a second position, thus breaking the seal between the rotatable cover and the stationary cover.
5. The covered sample container is then placed in its receptacle on the mixer apparatus, and a sleeve is positioned over the syringe to hold the syringe, inner cover, and dispersing element in place.
6. The mixer apparatus is turned on or activated so that the specimen container is rotated in relation to the dispersing element. This rotation occurs at a speed and time chosen by the technician which is sufficient to disperse clumps and mucous in the sample and to disperse cells throughout the sample.
7. At a predetermined time, the mixer is turned off or de-activated, and the particulate matter separation assembly can be removed from the mixer.
8. The plunger on the syringe is then withdrawn, drawing particulate matter containing fluid through the filter assembly. This step may be repeated, as desired.
9. Once particulate matter is captured on the collection surface, the pump assembly is disengaged, exposing the collection site.
10. The collection site may then be placed in contact with a microscope slide. Any particulate matter on the collection site is then transferred to the microscope slide, where it can be fixed, etc., using conventional cytological or histological techniques.
11. If desired, another microscope slide can be prepared using the same specimen sample, using a new filter assembly.

The inventors have performed steps E through K in about 2 minutes, as compared in to the Saccomanno process that takes 15 minutes to prepare the sample without filtering the particulate matter from the fluid.

According to another aspect of the present invention, the matter collection apparatus may also include additional modules, removable or integrated, for treating the fluid. For example, the fluid may be treated with a matter collection module, in combination with a debris removal module, a chromatography module, and assay module, or combinations of these and other devices. These and other modules or treatment protocols provide features that may be desirable to incorporate into a sample preparation apparatus according to the invention.

The matter collection apparatus or module described above may be used in combination with other suitable filtration or treatment devices. Exemplary devices include other debris and/or assay devices or modules that may be attached to housing 10. Typically, these additional modules will include a housing having an inlet and an outlet, and will include a filtration, assay, or detection element positioned across the fluid flow path in the housing. For example, the apparatus may comprise a housing including inlet and outlet ports defining a flow path between the inlet and the outlet; a filter positioned across the flow path; and a freely movable chromatography/assay element, such as substrate beads, positioned on the outlet side of the filter. The chromatography/assay element can freely mix with the matter in the fluid, capture the matter, and can then be assayed for the presence of the matter. Suitable devices include those disclosed in U.S. Pat. Nos. 4,953,561; 5,224,489; 5,016,644; 5,139,031; 5,301,685; 5,042,502; and 5,137,031.

Included within the scope of the present invention is producing a single slide from a patient sample, producing multiple slides from a single patient sample, or producing multiple slides from multiple patient samples. It is intended that a patient sample may be processed in a single shot, batch, or continuous manner. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the preparation does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatic patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is aesthetic, possibly reducing eyestrain.

Also, captured microorganisms can be cultured in culture medium. After a monolayer of cells has been collected in the cytology collection apparatus, fluid may be used to back-flush the collection site, thereby transferring any collected microorganisms from the collection site.

In bacteria testing, the first porous medium can be used for culturing with a Qualture device (not shown) to determine the presence of specific bacteria colonies. The Qualture device is a plastic capsule containing a filter membrane and four nutrient pads of dehydrated, selective media The Qualture technique is more sensitive than the agar plate method and more rapid in determining a presumptive diagnosis. The device screens, isolates and presumptively diagnoses bacterial isolates in one step most often in 4–6 hours. Tests have demonstrated that recovery from fifty milliliters of fluid is excellent and sensitive.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

In accordance with the present invention, the apparatus and method of the invention may be used to process sputum, and in particular, to replace the complex, time-consuming Saccomanno method of processing sputum. The apparatus and method of the invention are thus suitable for screening lung cancer samples and gynecological samples.

In some embodiments of the invention, it may be desirable to use a fixative solution in processing the specimen sample. Any commercially available fixative solution may be used with the apparatus and method of the present invention. A preferred fixative composition according to the invention includes one or more solvents, preferably an alkanol, between about 35% and about 45% by volume; ketone, between about 2% and about 3% by volume; a diluent, preferably a diol or triol, from about 1% to about 3% by volume; a crosslinker, preferably an aldehyde, from about 0.2% to about 4% by volume; glycerol, from about 0.5% to about 2% by volume; one or more detergents and/or dispersing agents, preferably non-ionic, from about 0.01% to about 0.05% by volume; and a buffer, from about 45 to about 65% by volume. In a preferred embodiment of the invention, the pH of the composition is between about 4 and about 7.

Table 1 summarizes the range and preferred concentrations of the components of a fixative formulation according to the present invention.

TABLE 1

| Component | range (by volume, %) | preferred (by volume, %) | example |
|---|---|---|---|
| solvent | 35–45 | 37–42 | alcohol |
| ketone | 2.0–3.0 | 2.1–2.4 | acetone |
| cell coating | 1.0–3.0 | 1.6–1.9 | PEG |
| polyol | 0.5–2.0 | 0.8–1.2 | glycerol |
| crosslinker | 0.2–4.0 | 0.6–0.8 | Formaldehyde glutaraldehyde |
| detergent | 0.01–0.05 | 0.02 | Nonidet P40 |

TABLE 1-continued

| Component | range (by volume, %) | preferred (by volume, %) | example |
|---|---|---|---|
| buffer | 45–65 | 50–55 | Tris |
| Mucolytic agent | 0.1–1.0 (grams %) | 0.2–0.5 (grams %) | dithiothreitol acetylcysteine |

An exemplary formulation of a composition for a fixative formulation that is useful with the present invention comprises about 40% by volume of alcohol (e.g., isopropanol and methanol), about 2–3% acetone, about 1.0–3.0% polyethylene glycol; about 2% by volume of formaldehyde (e.g., commercially available as formalin, a 3–37% v/v solution in water, sometimes including methyl alcohol); and about 58% by volume of buffer (e.g., Tris). The preferred pH of this formulation is about 5.0±0.5.

Another useful formulation is 40% alcohol (methanol and isopropanol); 2.2% acetone; 1.8% polyethylene glycol (PEG); 0.7% formaldehyde; 1% glycerol; 0.02% Nonidet P40; and 54% Tris Buffer (pH 7.4–7.8). All amounts are approximate percentages by volume.

What is claimed is:

1. A method for mixing and processing a sample in a specimen container having a cover and a dispersing element in the specimen container, the sample including particulate matter in a fluid, characterized in that the dispersing element is fixed relative to the cover, and the cover is rotatable relative to the specimen container, the method comprising:

placing the specimen container in a receptacle on a mixer apparatus;

engaging the cover for relative rotation with respect to the specimen container;

activating the mixer apparatus so that the specimen container is rotated in relation to the cover, whereby the particulate matter is dispersed throughout the sample by the relatively rotating dispersing element;

deactivating the mixer;

drawing the sample containing dispersed particulate matter through a filter assembly located in a housing atop the cover, whereby the particulate matter is captured in a substantially uniform layer on a collection surface;

opening the housing to expose the layer of particulate matter on the collection surface; and placing the exposed layer of particulate matter in contact with a microscope slide whereby the captured particulate matter is transferred from the collection site to the microscope slide.

2. The method according to claim 1, wherein the cover includes a first portion rotatable with respect to the specimen container, a second portion fixable with respect to the specimen container, and a frangible seal between the first portion and the second portion, the method further comprising the step of breaking said seal before placing the specimen container in the receptacle so that said first and second portions can rotate relative to one another.

3. The method according to claim 1 or claim 2, wherein the cover includes a pump in fluid communication with the sample in the specimen container, and the step of drawing the sample containing dispersed particulate matter through the filter assembly comprises activating the pump to create a suction in the specimen container.

4. The method according to claim 3, wherein the pump includes a syringe, and the step of drawing the sample comprises pulling the plunger of the syringe.

5. The method according to claim 4, further comprising removing the specimen container and the cover from the mixer after deactivating the mixer.

6. The method according to claim 5, further comprising fixing the captured particulate matter to the microscope slide.

7. The method according to claim 4, further comprising fixing the captured particulate matter to the microscope slide.

8. The method according to claim 3, further comprising fixing the captured particulate matter to the microscope slide.

9. The method according to claim 3, further comprising removing the specimen container and the cover from the mixer after deactivating the mixer.

10. The method according to claim 1 or claim 2, further comprising fixing the captured particulate matter to the microscope slide.

11. The method according to claim 1 or claim 2, further comprising removing the specimen container and the cover from the mixer after deactivating the mixer.

12. The method according to claim 1, further comprising:
replacing the filter assembly with a second filter assembly;
drawing the sample containing dispersed particulate matter through the second filter assembly, whereby the particulate matter is captured on a second collection surface; and
placing the second collection site in contact with a second microscope slide whereby the captured particulate matter is transferred from the second collection site to the second microscope slide.

13. The method according to claim 12, further comprising fixing the captured particulate matter to the each microscope slide.

* * * * *